US012740690B2

(12) United States Patent
Binmoeller et al.

(10) Patent No.: US 12,740,690 B2
(45) Date of Patent: Sep. 22, 2026

(54) SUTURE TIGHTENING DEVICE

(71) Applicants: MICRO-TECH (NANJING) CO., LTD., Jiangsu (CN); Kenneth F. Binmoeller, Rancho Santa Fe, CA (US)

(72) Inventors: Kenneth F. Binmoeller, Rancho Santa Fe, CA (US); Hongyan Jin, Jiangsu (CN); Xiaojun Ma, Jiangsu (CN)

(73) Assignees: MICRO-TECH (NANJING) CO., LTD., Jiangsu (CN); Kenneth F. Binmoeller

(*) Notice: Subject to any disclaimer, the term of this patent is extended or adjusted under 35 U.S.C. 154(b) by 128 days.

(21) Appl. No.: 18/797,348

(22) Filed: Aug. 7, 2024

(65) Prior Publication Data

US 2025/0057396 A1 Feb. 20, 2025

(30) Foreign Application Priority Data

Aug. 15, 2023 (CN) ......................... 202311032056.0
Aug. 15, 2023 (CN) ......................... 202322200881.9

(51) Int. Cl.
*A61B 1/00* (2006.01)
*A61B 17/04* (2006.01)

(52) U.S. Cl.
CPC .. *A61B 1/00121* (2013.01); *A61B 2017/0496* (2013.01)

(58) Field of Classification Search
CPC ........ A61B 1/00121; A61B 2017/0496; A61B 2017/00296; A61B 2017/00407; A61B 2017/00477; A61B 1/00133; A61B 1/018; A61B 17/0483; A61B 1/00137
See application file for complete search history.

(56) References Cited

U.S. PATENT DOCUMENTS 5,350,385 A * 9/1994 Christy ............ A61B 17/06109 606/139
2018/0146843 A1* 5/2018 Smith ................. A61B 8/4209

* cited by examiner

*Primary Examiner* — Richard G Louis
(74) *Attorney, Agent, or Firm* — BCF LLP

(57) ABSTRACT

Provided is a suture tightening device, including: a first thread take-up wheel, a second thread take-up wheel, and a thread gear support detachably connected to an endoscope handle, wherein the first thread take-up wheel is arranged at a space from the second thread take-up wheel, and the first thread take-up wheel and the second thread take-up wheel are separately in rotatable connection to the thread gear support.

17 Claims, 7 Drawing Sheets b
a
321 322
312 311
320
310

SUTURE TIGHTENING DEVICE

CROSS-REFERENCE TO RELATED APPLICATION

The present disclosure claims priority to Chinese Patent Applications CN202322200881.9 entitled "SUTURE TIGHTENING DEVICE" filed on Aug. 15, 2023, and CN202311032056.0 entitled "CLAMPING MECHANISM AMD SUTURE TIGHTENING DEVICE" filed on Aug. 15, 2023, the entire contents of which are incorporated herein by reference as part of the present disclosure.

TECHNICAL FIELD

The present disclosure relates to the technical field of medical suture apparatus, and particularly relates to a suture tightening device.

BACKGROUND ART

Referring to FIG. 10 and FIG. 11, a tightening pulley 900 in the prior art is mounted on an operating handle of a thread lock-cut mechanism 800. When the tightening pulley 900 is rotated to tighten a suture 700, a pulling force of the suture 700 will push the flexible thread lock-cut mechanism 800 to bend and move to a near end, so that a distance between the tightening pulley 900 and a jaw opening of the endoscope handle is shortened, which in turn is difficult to control a take-up (winding) length of the suture 700, such that it is difficult to close wound edges from each other. Additionally, when two single anchor mechanisms are used to suture tissues, two sutures are tightened by the same thread take-up wheel, so it is not possible to adjust the looseness or tightness of a single suture. It is difficult to ensure that a locking and cutting position of two sutures is in a center of the suture part, which may produce a technical problem of a deviation of the suture part. When tightening the suture and locking and cutting the suture, it is necessary to ensure that the thread lock-cut mechanism 800 remains stable relative to the endoscope handle, otherwise a tightening strength of the suture will be affected. Moreover, when operating, on the one hand, the operator needs to hold the endoscope handle, and on the other hand, the operator also needs to carry out operations such as taking up the thread, and locking and cutting. Since the endoscope handle in the prior art cannot fix other instruments, not only does it require additional persons to assist, but also the multiple persons are concentrated in one place to operate, which is easy to produce mutual interferences, thus affecting the accuracy of the surgical operation.

SUMMARY

An object of the present disclosure is to provide a suture tightening device to solve technical problems that a take-up length of the suture is difficult to control, and the tightening state of two sutures cannot be adjusted individually.

In a first aspect, the present disclosure provides a suture tightening device, including: a first thread take-up wheel (thread winding roller/wheel), a second thread take-up wheel, and a thread gear support detachably connected to an endoscope handle, wherein the first thread take-up wheel is arranged at a space from the second thread take-up wheel, and the first thread take-up wheel and the second thread take-up wheel are separately in rotatable connection to the thread gear support.

In an optional embodiment, the first thread take-up wheel and the second thread take-up wheel both include: a gear body, a first gear disk, and a second gear disk, wherein the gear body, the first gear disk, and the second gear disk are arranged coaxially, wherein the first gear disk is arranged at a space from the second gear disk; the first gear disk and the second gear disk are separately connected to the gear body; and a thread winding groove is formed between the first gear disk and the second gear disk.

In an optional embodiment, the first thread take-up wheel and/or the second thread take-up wheel are provided with a thread clamping groove.

In an optional embodiment, the first thread take-up wheel and/or the second thread take-up wheel are provided with a plurality of position limitation parts, and the plurality of position limitation parts are arranged at intervals around a gear shaft.

In an optional embodiment, elastic position limitation members are mounted on the thread gear support; the clastic position limitation members are fitted to the position limitation parts; and the elastic position limitation members tend to keep fit with the position limitation parts.

In an optional embodiment, the elastic position limitation members support the first thread take-up wheel and the second thread take-up wheel, so as to prevent the first thread take-up wheel and the second thread take-up wheel from rotating back, and to keep sutures to be tightened extending from the endoscope handle to the first thread take-up wheel and the second thread take-up wheel respectively;

the position limitation parts are provided with beveled surfaces, wherein when the first thread take-up wheel or the second thread take-up wheel is rotated to tighten the sutures, the beveled surfaces push the elastic position limitation members, so that the elastic position limitation members remove from the position limitation parts; or when the clastic position limitation members incline along a circumference of the thread take-up wheel, and the first thread take-up wheel or the second thread take-up wheel is rotated to tighten the sutures, the position limitation parts push the elastic position limitation members, so that the elastic position limitation members slip out relative to the position limitation parts.

In an optional embodiment, an angle exists between an axis of the first thread take-up wheel and an axis of the second thread take-up wheel, and a bisector of the angle between the axis of the first thread take-up wheel and the axis of the second thread take-up wheel intersects an axis of an endoscope working cavity of the endoscope handle.

In an optional embodiment, the thread gear support is connected with a bandage, and the bandage is bound to the endoscope handle.

In an optional embodiment, a first clamping arm and a second clamping arm are movably mounted on the thread gear support, and a clamping area is formed between the first clamping arm and the second clamping arm.

In an optional embodiment, the first clamping arm is provided with a first tooth part; the second clamping arm is provided with a second tooth part fitted to the first tooth part; the first tooth part cooperates with the second tooth part; and the clamping area is formed between the first tooth part and the second tooth part.

In an optional embodiment, one end of the first clamping arm and one end of the second clamping arm are separately pivoted to the thread gear support, and the other end of the first clamping arm is opposite to the other end of the second clamping arm to form the clamping area.

In an optional embodiment, the thread gear support is elastic, and the thread gear support squeezes the first clamping arm and the second clamping arm, so that the first clamping arm and the second clamping arm tend to form an angle.

In an optional embodiment, in an unlocking state, an opening is formed on one side of the clamping area, wherein a clamped part of the second surgical instrument enters the clamping area through the opening along a first direction, and the first clamping arm and the second clamping arm are pushed to simultaneously switch to a locking state, so that an opening degree of the opening is reduced or closed; and when the clamped part, the first clamping arm, or the second clamping arm is operated in a direction opposite to the first direction, the first clamping arm and the second clamping arm are simultaneously switched to the unlocking state, so that the clamped part is removed via the opening.

In an optional embodiment, the first clamping arm is provided with a first position limitation groove; the second clamping arm is provided with a second position limitation groove opposite to the first position limitation groove; and the clamping area is formed between the first position limitation groove and the second position limitation groove, wherein in the locking state, the thread gear support squeezes the first clamping arm and the second clamping arm to deflect to a first direction, and the second surgical instrument is clamped between the first position limitation groove and the second position limitation groove; and in the unlocking state, the thread gear support squeezes the first clamping arm and the second clamping arm to deflect to a second direction, so as to enlarge the opening degree of the clamping area between the first position limitation groove and the second position limitation groove.

In an optional embodiment, the thread gear support is provided with a locking and position limitation structure, or, the first clamping arm and/or the second clamping arm are provided with the locking and position limitation structure, wherein the locking and position limitation structure is configured to prevent the first clamping arm and the second clamping arm from continuing to deflect to the first direction during the locking state.

In an optional embodiment, the thread gear support is further provided with a crossbar, and the crossbar is provided with an avoiding groove, wherein the avoiding groove is configured to accommodate the second surgical instrument, and/or to prevent the second surgical instrument from continuing to move to the first direction.

The embodiments of the present disclosure include the following beneficial effects. The thread gear support is detachably connected to the endoscope handle; the first thread take-up wheel is arranged at a space from the second thread take-up wheel; and the first thread take-up wheel and the second thread take-up wheel are separately in rotatable connection to the thread gear support. The first thread take-up wheel and the second thread take-up wheel can separately tighten two sutures, and can adjust one of two sutures to be tight or loose individually, which in turn can avoid the locking and cutting position of the two sutures from deflecting. Additionally, the first thread take-up wheel and the second thread take-up wheel separately drive the suture to tighten, which does not cause the thread lock-cut mechanism to bend. It not only does not interfere with the manipulation of the thread lock-cut mechanism, but also facilitates to controlling the take-up length of the suture.

In order to make the above purposes, features, and advantages of the present disclosure more obvious and understandable, the preferred embodiments, together with the drawings, are described in detail as follows.

BRIEF DESCRIPTION OF DRAWINGS

In order to more clearly illustrate specific embodiments of the present disclosure or technical solutions of the related arts, the drawings to be used in descriptions of the specific embodiments or the related arts will be briefly introduced below. It is obvious that the drawings in the following description are some embodiments of the present disclosure. For a person of ordinary skill in the art, other drawings can be obtained from these drawings without inventive efforts.

Figure 1:
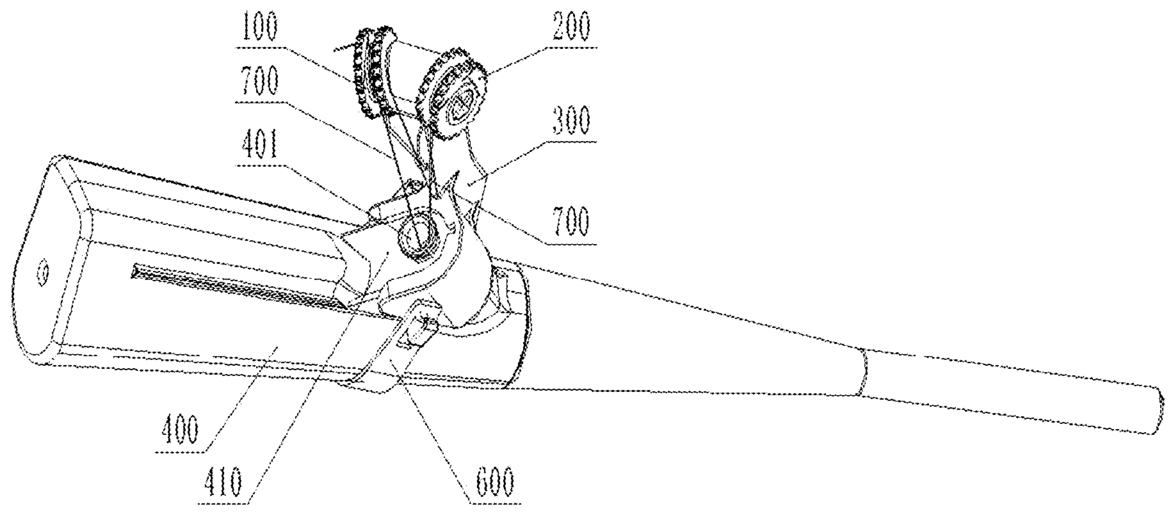
FIG. 1 shows a schematic diagram of a suture tightening device and an endoscope handle provided by the embodiments of the present disclosure.

Reference numbers: 100—first thread take-up wheel; 101—thread winding groove; 102—thread clamping groove; 103—position limitation part; 131—beveled surface; 110—gear body; 120—first gear disk; 130—second gear disk; 200—second thread take-up wheel; 300—thread gear support; 301—position limitation groove; 302—convex edge part; 303—avoiding groove; 304—locking and position limitation structure; 310—first clamping arm; 311—first tooth part; 312—first position limitation groove; 320—second clamping arm; 321—second tooth part; 322—second position limitation groove; 330—crossbar; 400—endoscope handle; 401—endoscope working cavity; 410—convex platform; 500—clastic position limitation member; 600—bandage; 700—suture; 800—thread lock-cut mechanism; 810—outer tube; and 900—tightening pulley.

DETAILED DESCRIPTION OF EMBODIMENTS

The technical solutions of the present disclosure will be clearly and completely described below in conjunction with the drawings. It is clear that the described embodiments are partial embodiments of the present disclosure, and not all of the embodiments. Based on the embodiments of the present disclosure, all other embodiments obtained by a person of ordinary skill in the art without inventive efforts, fall within the scope of protection of this disclosure.

In the description of the present disclosure, it should be noted that orientations or positional relationships indicated by terms such as "center", "up", "down", "left", "right", "vertical", "horizontal", "inside", "outside" are the orientations or positional relationships based on the drawings, and are only intended to facilitate the description of the present disclosure and simplify the description, and are not to indicate or imply that the device or element referred to must have a particular orientation, be constructed and operated in a particular orientation, and therefore should not to be understood as limitations of the present disclosure. Furthermore, the terms "first", "second", and "third" are used for descriptive purposes only, and are not to be understood as indicating or implying relative importance. If there are not individually labeled, physical quantities in formulas shall be understood as the basic quantities in the basic units of the International System of Units, or derived quantities derived from the basic quantities by mathematical operations such as multiplication, division, differentiation, or integration.

In the description of the present disclosure, it is to be noted that unless otherwise expressly specified and limited, the terms "mount", "connect", and "link" shall be understood in a broad sense, for example, it can be a fixed connection, a detachable connection, or an integral connection; it can be a mechanical connection, or an electrical connection; it can be a direct connection, or an indirect connection through an intermediate medium, or a communication inside two elements. For those of ordinary skill in the art, the specific meaning of the above terms in the present disclosure may be understood in specific conditions.

As shown in FIG. 1, FIG. 3, FIG. 4 and FIG. 7, the embodiments of the present disclosure provide a suture tightening device, including: a first thread take-up wheel 100, a second thread take-up wheel 200, and a thread gear support 300 detachably connected to an endoscope handle 400, wherein the first thread take-up wheel 100 is arranged at a space from the second thread take-up wheel 200, and the first thread take-up wheel 100 and the second thread take-up wheel 200 are separately in rotatable connection to the thread gear support 300.

When taking up the thread, two sutures 700 are wound around the first thread take-up wheel 100 and the second thread take-up wheel 200 in one-to-one correspondence, and two sutures 700 can be separately tightened by rotating the first thread take-up wheel 100 and second thread take-up wheel 200. The first thread take-up wheel 100 and the second thread take-up wheel 200 can rotate individually, so that one of two sutures 700 can be adjusted to be tight or loose, which in turn can avoid the locking and cutting position of two sutures 700 from deflecting. Additionally, the thread gear support 300 can be mounted to the endoscope handle 400, wherein distances from an endoscope working cavity 401 of an endoscope handle 400 to the first thread take-up wheel 100 and the second thread take-up wheel 200 remain unchanged, which can avoid the take-up operation from interfering with other devices, and facilitate to controlling the take-up length of the suture 700.

The endoscope handle 400 is taken as a first surgical instrument, and the second surgical instrument is clamped and fixed by the clamping area, so as to keep the first surgical instrument and the second surgical instrument relatively stable. It does not need the operator to hold and fix the second surgical instrument by a single hand, and it does not need to limit and fix the second surgical instrument with the assistance of other person, which can avoid the operator from being disturbed or can avoid a plurality of surgical instruments from interfering with each other when operating.

Compared with the prior art, an outer tube 810 of the thread lock-cut mechanism 800 can be clamped in the clamping area between the first clamping arm 310 and the second clamping arm 320, so as to keep the thread lock-cut mechanism 800 stable relative to the endoscope handle 400, which in turn avoids the thread lock-cut mechanism 800 from deviating during the process of tightening the suture, and is beneficial for the operator to take up and lock and cut the suture by a single hand. The clamping area can also be configured to clamp other endoscope surgical instruments, so to ensure that the position of the second surgical instrument remains stable relative to the endoscope handle 400, thereby reducing the difficulty of operation for the operator.

Figure 2:
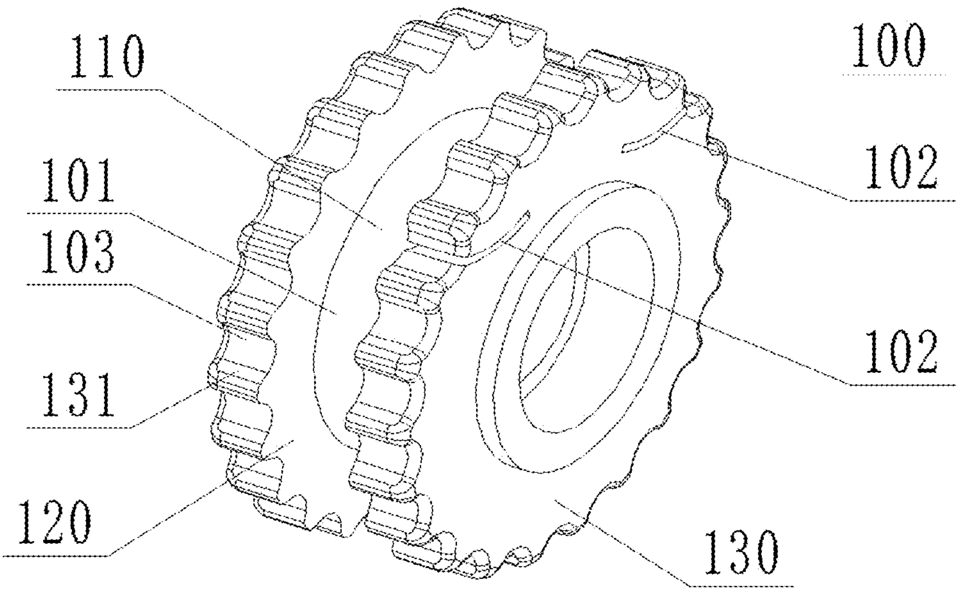
FIG. 2 shows a schematic diagram of a first thread take-up wheel of a suture tightening device provided by the embodiments of the present disclosure.

As shown in FIG. 1 and FIG. 2, in the embodiments of the present disclosure, the first thread take-up wheel 100 and the second thread take-up wheel 200 both include: a gear body 110, a first gear disk 120, and a second gear disk 130, wherein the gear body 110, the first gear disk 120, and the second gear disk 130 are arranged coaxially, wherein the first gear disk 120 is arranged at a space from the second gear disk 130; the first gear disk 120 and the second gear disk 130 are separately connected to the gear body 110; and a thread winding groove 101 is formed between the first gear disk 120 and the second gear disk 130.

When taking up the thread, a lead thread is used to lead the suture 700 out of the endoscope working cavity 401, and the suture 700 is wound around the gear body 110, so that the suture 700 can be limited in the thread winding groove 101 by the first gear disk 120 and the second gear disk 130, so as to avoid the suture 700 from falling off the gear body 110. The length of the suture 700 wound around the first thread take-up wheel 100 and the second thread take-up wheel 200 can be separately controlled by rotating the first thread take-up wheel 100 and the second thread take-up wheel 200, so as to realize the adjustment for the take-up length.

Furthermore, the first thread take-up wheel 100 and/or the second thread take-up wheel 200 are provided with a thread clamping groove 102.

In an optional embodiment, the thread clamping groove 102 is arranged on the first thread take-up wheel 100, or the thread clamping groove 102 is arranged on the second thread take-up wheel 200, or the first thread take-up wheel 100 and the second thread take-up wheel 200 are both provided with the thread clamping grooves 102. The end of the suture 700 passes through the thread clamping groove 102, and the suture 700 is clamped by the thread clamping groove 102, so as to avoid the suture 700 from loosening and falling off.

As shown in FIG. 1, FIG. 2, FIG. 3, FIG. 4, FIG. 12, and FIG. 13, the first thread take-up wheel 100 and/or the second thread take-up wheel 200 are provided with a plurality of position limitation parts 103, wherein the plurality of position limitation parts 103 are arranged at intervals around a gear shaft.

In an optional embodiment, the plurality of position limitation parts 103 are arranged on the first thread take-up wheel 100, or the plurality of position limitation parts 103 are arranged on the second thread take-up wheel 200, or the first thread take-up wheel 100 and the second thread take-up wheel 200 are both provided with the plurality of position limitation parts 103. The position limitation parts 103 are configured as toothed parts or grooves, and the plurality of position limitation parts 103 form knurling structures around the circumferences of the first thread take-up wheel 100 and the second thread take-up wheel 200, so as to increase a friction force when touching the first thread take-up wheel 100 and the second thread take-up wheel 200 by the hand, which avoids slipping when the first thread take-up wheel 100 and the second thread take-up wheel 200 are operated to rotate by the hand.

Additionally, an elastic position limitation member 500 is mounted on the thread gear support 300; the clastic position limitation member 500 is fitted to the position limitation parts 103; and the clastic position limitation member 500 tends to keep fit with the position limitation parts 103. The elastic position limitation member 500 abuts against one of the position limitation parts 103 in a resilience state, so as to lock the first thread take-up wheel 100 and the second thread take-up wheel 200, thereby realizing the determining of the tightening size of the suture 700.

In the embodiment, the clastic position limitation member 500 supports the first thread take-up wheel 100 and the second thread take-up wheel 200, so as to prevent the first thread take-up wheel 100 and the second thread take-up wheel 200 from rotating back, and to keep sutures 700 to be tightened extending from the endoscope handle 400 to the first thread take-up wheel 100 and the second thread take-up wheel 200 separately.

Figure 3:
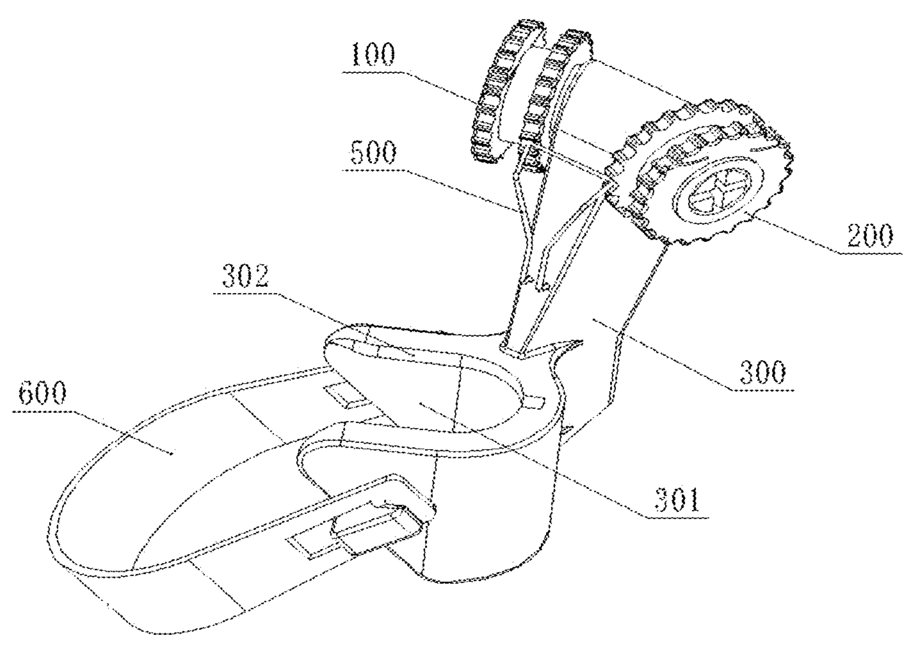
FIG. 3 shows a schematic diagram of a suture tightening device provided by the embodiments of the present disclosure.
Figures 7, 8:
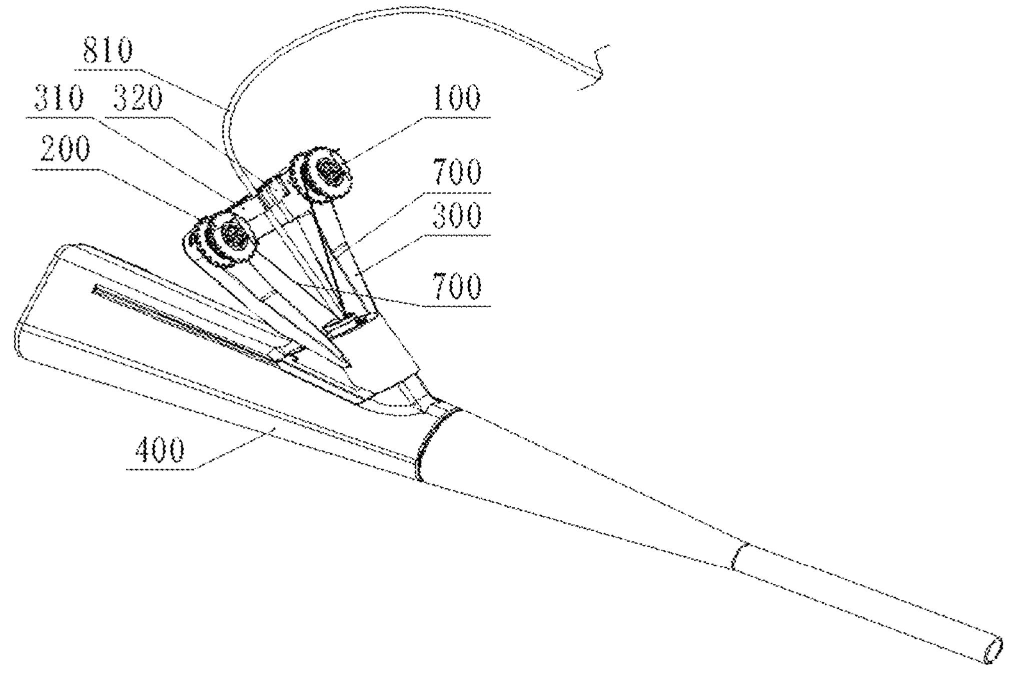
FIG. 7 shows a schematic diagram of a suture tightening device and endoscope handle provided by the embodiments of the present disclosure.
FIG. 8 shows a schematic diagram of a first clamping arm and a second clamping arm of a suture tightening device provided by the embodiments of the present disclosure.
Figure 12:
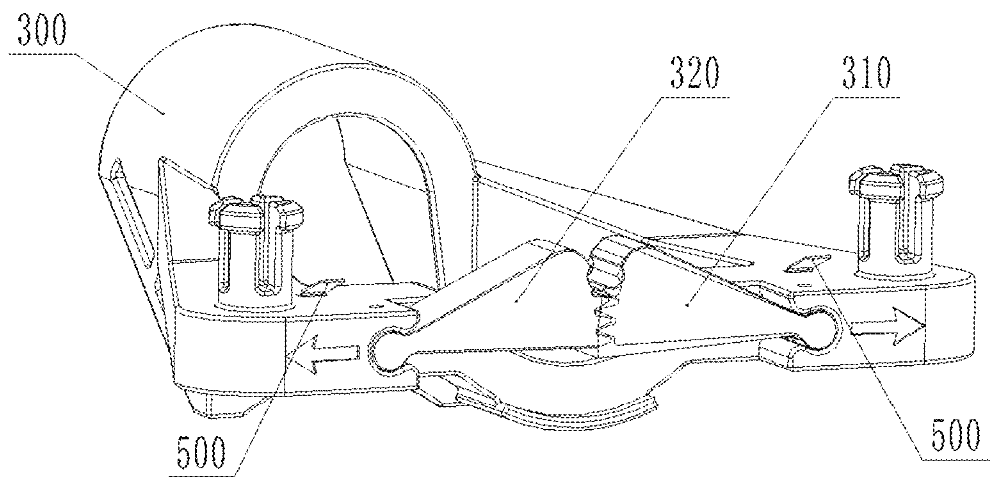
FIG. 12 shows a schematic diagram of a thread gear support and an clastic position limitation member of a suture tightening device provided by the embodiments of the present disclosure.
Figure 13:
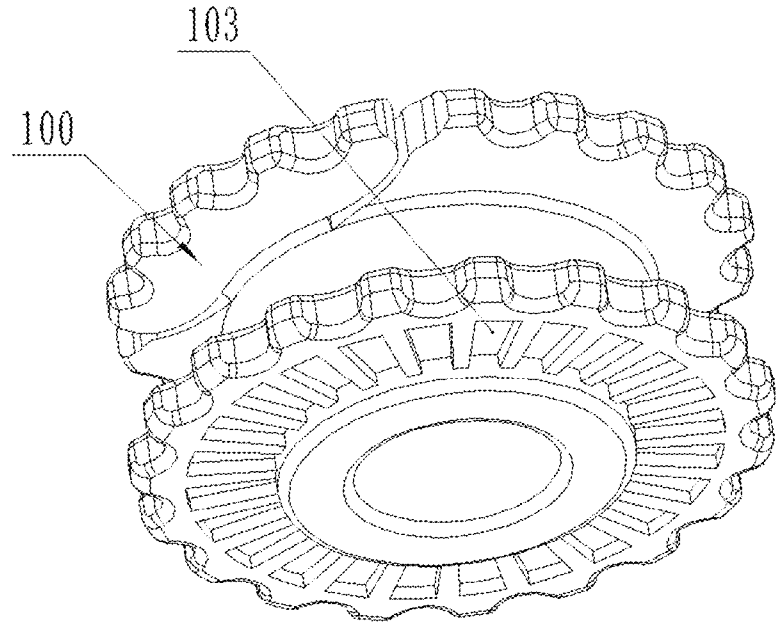
FIG. 13 shows a schematic diagram of another first thread take-up wheel in a suture tightening device provided by the embodiments of the present disclosure.

Referring to FIG. 1, FIG. 2, and FIG. 3, the position limitation part 103 is provided with a beveled surface 131, wherein when the first thread take-up wheel 100 or the second thread take-up wheel 200 is rotated to tighten the suture 700, the beveled surface 131 pushes the elastic position limitation member 500, so that the elastic position limitation member 500 removes from the position limitation part 103; or referring to FIG. 7, FIG. 12, and FIG. 13, when the clastic position limitation member 500 inclines along a circumference of the thread take-up wheel, and the first thread take-up wheel 100 or the second thread take-up wheel 200 is rotated to tighten the suture 700, the position limitation part 103 pushes the elastic position limitation member 500, so that the elastic position limitation member 500 slips out relative to the position limitation part 103.

As shown in FIG. 1, FIG. 2, and FIG. 3, when the first thread take-up wheel 100 and the second thread take-up wheel 200 are rotated by an external force, the elastic position limitation member 500 is pushed by the beveled surface 131, so the end of the elastic position limitation member 500 can depart from the position limitation part 103. In this way, the first thread take-up wheel 100 and the second thread take-up wheel 200 can continue to rotate, so as to continue to pull the suture 700 for the tightening operation. When it is necessary to readjust the tightening states of two sutures 700, the first thread take-up wheel 100 and the second thread take-up wheel 200 can be unlocked by manually operating the elastic position limitation member 500. The first thread take-up wheel 100 and the second thread take-up wheel 200 are separately rotated under the action of the tightening force of the sutures 700, and then the elastic position limitation member 500 is released. The two sutures 700 can be readjusted to tighten again by separately rotating the first thread take-up wheel 100 and the second thread take-up wheel 200 again, so that the threads can be taken up again when the locking and cutting position of two suture 700 deflects.

Referring to FIG. 12 and FIG. 13, in an optional embodiment, the elastic position limitation member 500 is configured as an elastic plate mounted to the thread gear support 300; and the position limitation part 103 is configured as a plurality of protrusions or grooves arranged at intervals along the circumference of the thread take-up wheel, wherein the elastic plate inclines along the circumference of the thread take-up wheel, and the end of the elastic plate abuts against the position limitation part 103, so that the thread take-up wheel can be locked in a single direction.

As shown in FIG. 1, FIG. 2, and FIG. 3, an angle exists between an axis of the first thread take-up wheel 100 and an axis of the second thread take-up wheel 200, and a bisector of the angle between the axis of the first thread take-up wheel 100 and the axis of the second thread take-up wheel 200 intersects an axis of an endoscope working cavity 401 of the endoscope handle 400.

Specifically, two sutures 700 extending from the endoscope working cavity 401 separately extend to the first thread take-up wheel 100 and the second thread take-up wheel 200, and two sutures 700 directly face two thread winding grooves 101 respectively, which can avoid the first gear disk 120 and the second gear disk 130 from scraping the sutures 700, and enables the two sutures 700 to be smoothly wound around the first thread take-up wheel 100 and the second thread take-up wheel 200 respectively.

As shown in FIG. 1 and FIG. 3, the thread gear support 300 is connected with a bandage 600, wherein the bandage 600 is bound to the endoscope handle 400. The bandage 600 can be connected to the endoscope handle 400 by a fastener; or the bandage 600 can be provided with a magic tape, wherein the bandage 600 is fixed by the connection of the magic tape after the bandage 600 is connected to the thread gear support 300 and wound around the endoscope handle 400.

Furthermore, the bandage 600 can be made of elastic materials, and the thread gear support 300 can be fixed by binding the bandage 600, and the bandage 600 tends to contract, so that the thread gear support 300 can remain stable relative to the endoscope handle 400.

As shown in FIG. 1, FIG. 3, FIG. 4, FIG. 7, and FIG. 9, the thread gear support 300 is provided with a position limitation groove 301, and the endoscope handle 400 is provided with a convex platform 410 inserted into the position limitation groove 301. The endoscope working cavity 401 extends and passes through the convex platform 410, and the convex platform 410 is arranged in the position limitation groove 301, so that the thread gear support 300 can be positioned relative to the endoscope handle 400 when mounting the thread gear support 300.

Figure 6:
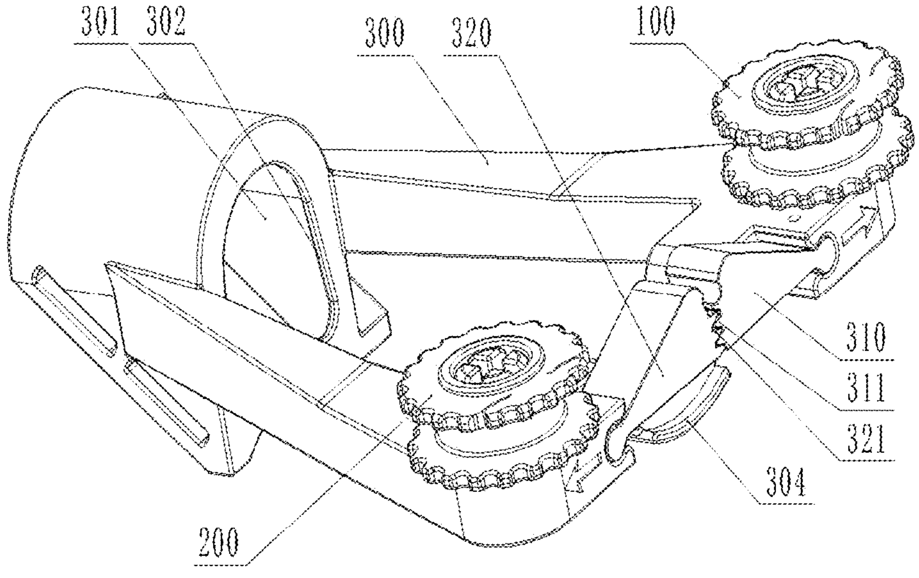
FIG. 6 shows a third schematic diagram of another suture tightening device provided by the embodiments of the present disclosure.
Figure 9:
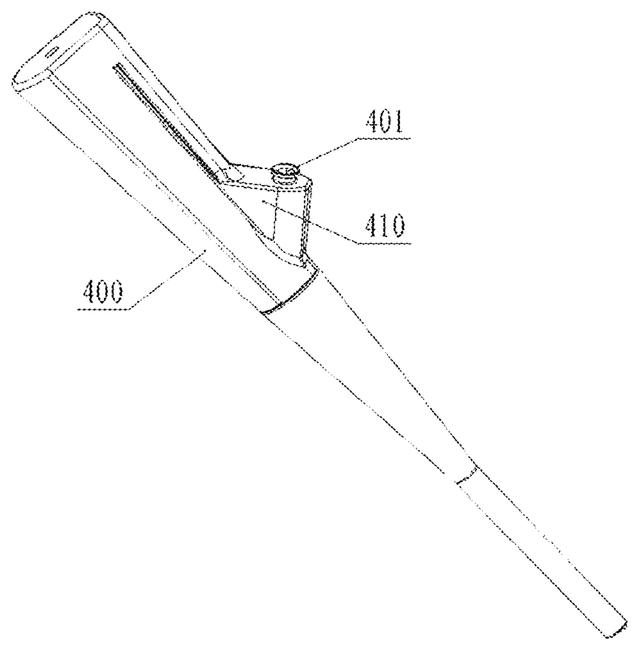
FIG. 9 shows a schematic diagram of an endoscope handle provided by the embodiments of the present disclosure.
Figure 10:
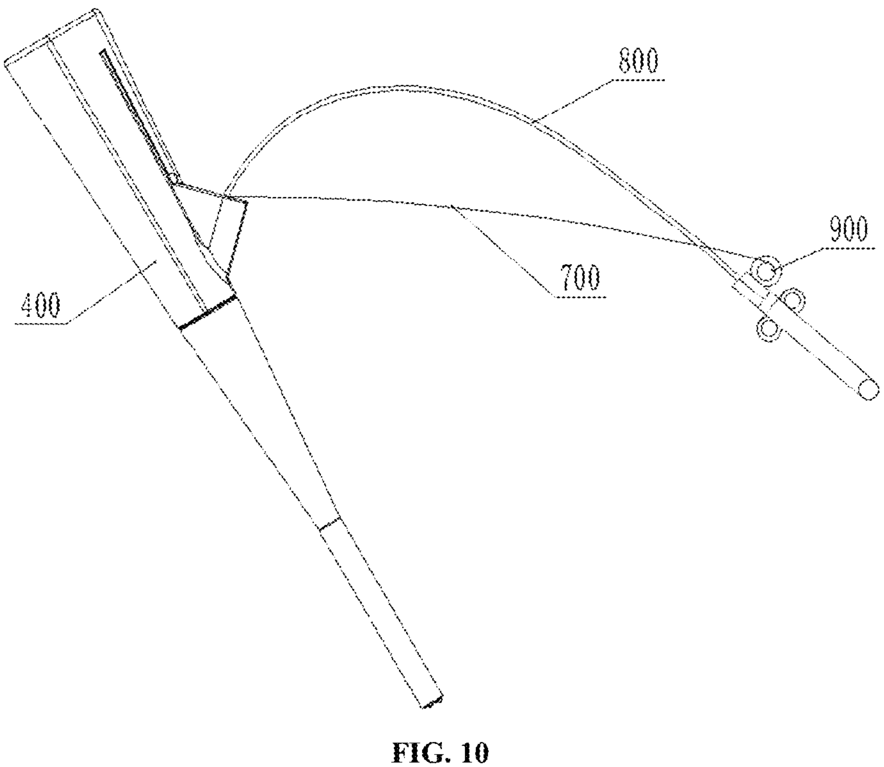
FIG. 10 shows a schematic diagram of an endoscope handle, suture, thread lock-cut mechanism, and tightening pulley in the prior art.
Figure 11:
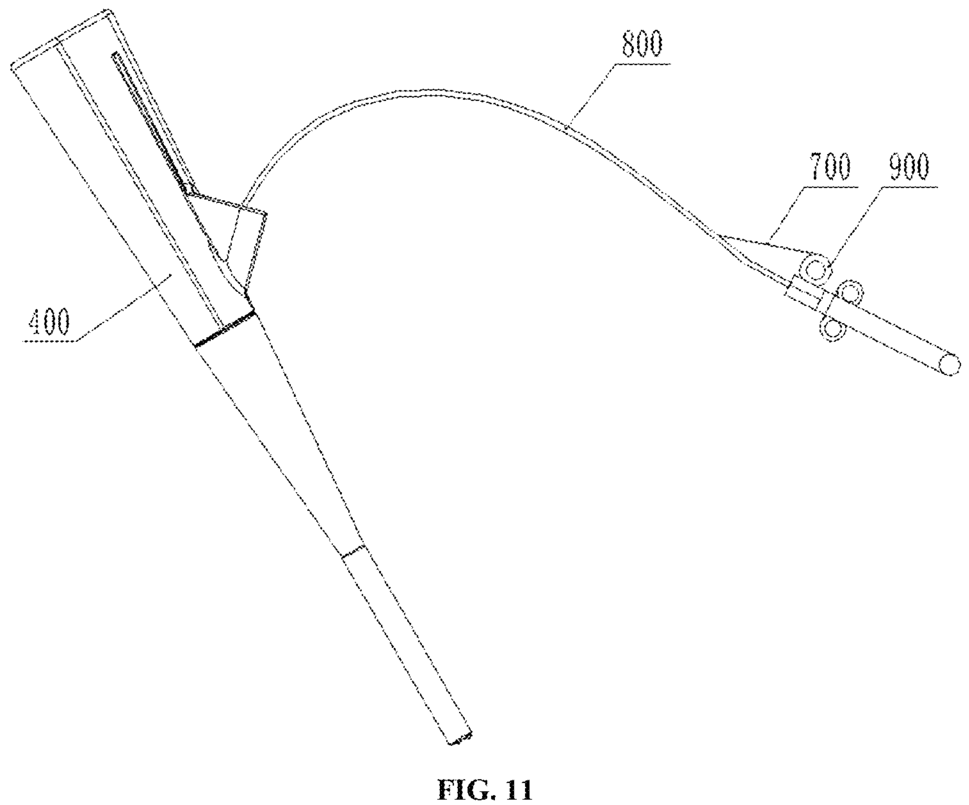
FIG. 11 shows a schematic diagram of the other endoscope handle, suture, thread lock-cut mechanism, and tightening pulley in the prior art.

As shown in FIG. 6 and FIG. 9, the thread gear support 300 is further provided with a convex edge part 302, and the convex edge part 302 abuts against a top surface of the convex platform 410, wherein the axis of the endoscope working cavity 401 is perpendicular to the top surface of the convex platform 410, and the convex edge part 302 abuts against the top surface of the convex platform 410, so that the thread gear support 300 can be positioned relative to the convex platform 410 in the axial direction of the endoscope working cavity 401, so that the thread gear support 300 is in a stable position.

As shown in FIG. 4, FIG. 5, FIG. 6, FIG. 7, and FIG. 8, the first clamping arm 310 and the second clamping arm 320 are movably mounted on the thread gear support 300, and the clamping area is formed between the first clamping arm 310 and the second clamping arm 320, wherein the clamping area can clamp the outer tube of the thread lock-cut mechanism, so as to ensure that the thread lock-cut mechanism is relatively stable during the process of taking up the thread.

Specifically, the first clamping arm 310 and the second clamping arm 320 can be configured as elastic components, so that the clamping area can be elastically clamped. Additionally, the first clamping arm 310 and the second clamping arm 320 can be connected to the thread gear support 300 by a slidable connection, or a hinge connection, etc. When the first clamping arm 310 and the second clamping arm 320 can be connected by the slidable connection, the first clamping arm 310 and the second clamping arm 320 can be driven by the elastic position limitation member, so that the outer tube of the thread lock-cut mechanism can be clamped between the first clamping arm 310 and the second clamping arm 320. When the first clamping arm 310 and the second clamping arm 320 can be slidably connected to the thread gear support 300 by the hinge connection, the thread gear support 300 can be provided with a mounting groove of rotating shaft; the first clamping arm 310 and the second clamping arm 320 are separately provided with rotating shaft parts; and two rotating shaft parts are arranged in two mounting grooves of the rotating shafts in one-to-one correspondence. On a section perpendicular to the rotating shaft axis, a central angle corresponding to mounting groove of the rotating shaft is larger than 180 degrees, so that the rotating shaft part can be limited in the mounting groove of the rotating shaft, and the first clamping arm 310 and the second clamping arm 320 can be separately driven to swing and rotate within a certain angular range.

Furthermore, the first clamping arm 310 is provided with a first position limitation groove 312, and the second clamping arm 320 is provided with a second position limitation groove 322 opposite to the first position limitation groove 312.

By adopting an elastic structure, the first clamping arm 310 and the second clamping arm 320 are driven to reset and lock, or the first clamping arm 310 and the second clamping arm 320 tend to be connected to each other in the locking state through a self-locking manner; and the outer tube 810 of the thread lock-cut mechanism 800 is clamped between the first position limitation groove 312 and the second position limitation groove 322, so as to ensure that the thread lock-cut mechanism 800 keeps stable relative to the thread gear support 300.

The first clamping arm 310 and the second clamping arm 320 can be unlocked by a manual operation, and the first clamping arm 310 and the second clamping arm 320 open opposite to each other in the unlocking state. In other words, the opening of the clamping area between the first clamping arm 310 and the second clamping arm 320 is enlarged, so as to enlarge the opening degree of the opening between the first position limitation groove 312 and the second position limitation groove 322, so that the outer tube 810 can be implanted or extracted.

Figure 5:
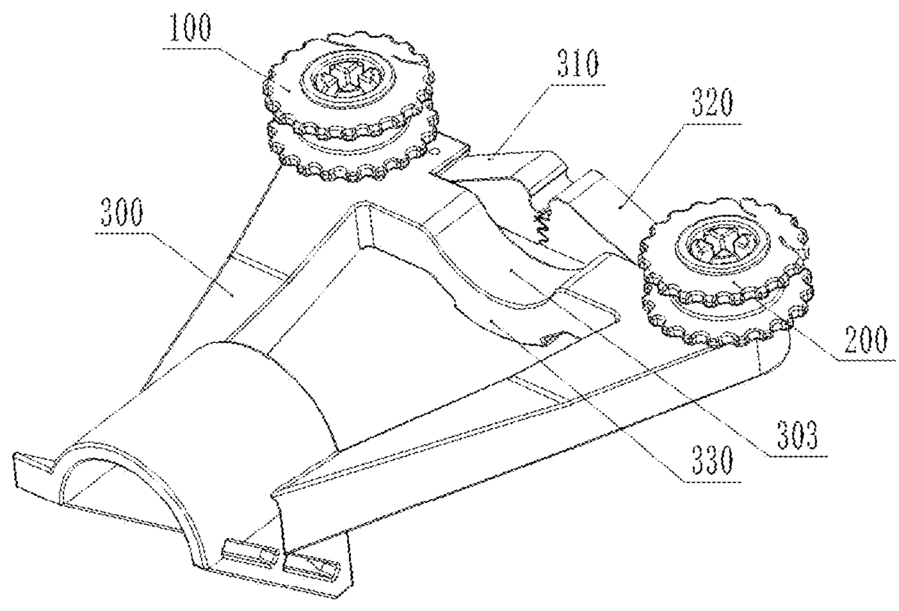
FIG. 5 is a second schematic diagram of another suture tightening device provided by the embodiments of the present disclosure.

As shown in FIG. 5, the thread gear support 300 is further provided with a crossbar 330, and the crossbar 330 is provided with an avoiding groove 303, wherein the avoiding groove 303 is configured to accommodate the second surgical instrument, or the avoiding groove 303 is configured to prevent the second surgical instrument from continuing to move to the first direction. In an optional embodiment, the avoiding groove 303 can also be configured to accommodate the second surgical instrument, and the bottom or side wall of the avoiding groove 303 is configured to prevent the second surgical instrument from continuing to move in the first direction. Preferably, the avoiding groove 303 directly faces the clamping area, and the axis of the avoiding groove 303 is located between the first clamping arm 310 and the second clamping arm 320. When the first clamping arm 310 and the second clamping arm 320 clamp the second surgical instrument (the outer tube of the thread lock-cut mechanism), the side wall of the second surgical instrument (the outer tube of the thread lock-cut mechanism) abuts against the crossbar 330. The first clamping arm 310 and the second clamping arm 320 clamp the outer tube together, and the outer tube maintains a tendency to abut against the crossbar 330, so that the first clamping arm 310 and the second clamping arm 320 are maintained at the dead point position, and thereby the outer tube can be maintained in the clamped and fixed state. When the outer tube needs to be unclamped, the first clamping arm 310 and the second clamping arm 320 are operated to swing by the external force, and the outer tube is moved away from the crossbar 330, so as to realize the unlocking, which in turn opens up the clamping area between the first clamping arm 310 and the second clamping arm 320, and thereby the outer tube of the thread lock-cut mechanism can be released. The second surgical instrument passes through the avoiding groove 303 and extends into the endoscope working cavity, which on the one hand makes the structure more compact, and on the other hand avoids the second surgical instrument from bending, so that the thread pulling operation in the locking and cutting operation can be smoother. The second surgical instrument can be the thread lock-cut mechanism 800 or other endoscope surgical instruments. Preferably, the shapes of the first position limitation groove 312, the second position limitation groove 322, and the avoiding groove 303 are fitted to the clamped part of the clamped instrument.

Furthermore, as shown in FIG. 6 and FIG. 8, the first clamping arm 310 is provided with a first tooth part 311; the second clamping arm 320 is provided with a second tooth part 321 fitted to the first tooth part 311; the first tooth part 311 cooperates with the second tooth part 321; and the clamping area is formed between the first tooth part 311 and the second tooth part 321, so that the first clamping arm 310 can be accurately aligned with the second clamping arm 320, so as to avoid the first clamping arm 310 from loosening relative to the second clamping arm 320, so that the first clamping arm 310 and the second clamping arm 320 can be better in the locking state at the dead point, and the stability of the clamped outer tube 810 can be improved.

Figure 4:
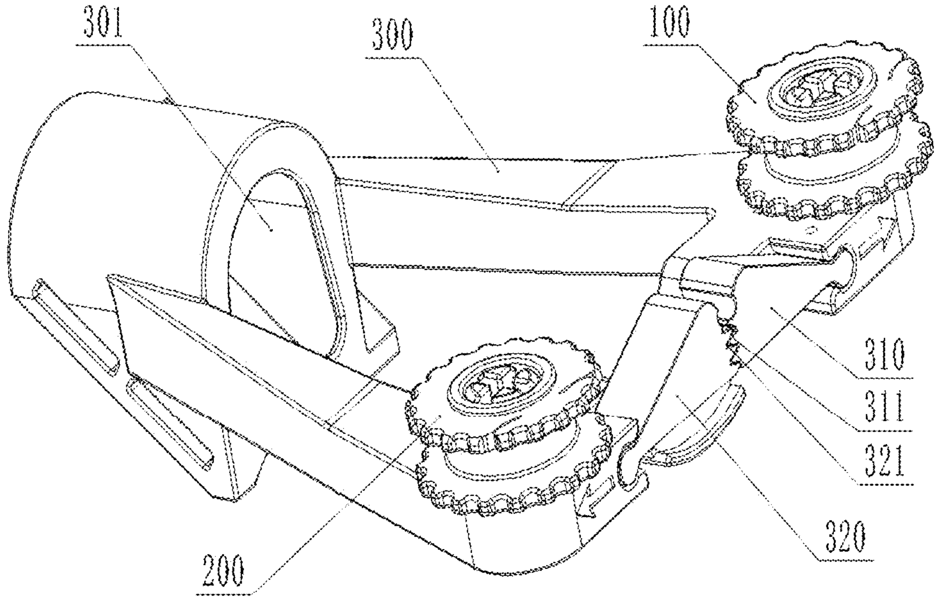
FIG. 4 shows a first schematic diagram of another suture tightening device provided by the embodiments of the present disclosure.

As shown in FIG. 4, FIG. 5, and FIG. 6, in an optional embodiment, one end of the first clamping arm 310 and one end of the second clamping arm 320 are separately hinged to the thread gear support 300, and the other end of the first clamping arm 310 is opposite to the other end of the second clamping arm 320 to form the clamping area. The thread gear support 300 is clastic, and the thread gear support 300 squeezes the first clamping arm 310 and the second clamping arm 320, so that the first clamping arm 310 and the second clamping arm 320 tend to form an angle. The thread gear support 300 is provided with the mounting groove of the rotating shaft, and the first clamping arm 310 and the second clamping arm 320 are separately provided with the rotating shaft part, wherein the two rotating shaft parts are arranged in mounting grooves of two rotating shafts in one-to-one correspondence. On the section perpendicular to the rotating shaft axis, the central angle corresponding to mounting groove of the rotating shaft is larger than 180 degrees, so that the rotating shaft part can be limited in the mounting groove of the rotating shaft, and so that the first clamping arm 310 and the second clamping arm 320 can swing and rotate in a certain angular range respectively. In a state that the first clamping arm 310 and the second clamping arm 320 are relatively straight, both the first clamping arm 310 and the second clamping arm 320 are squeezed by the thread gear support 300, so that a space between two rotating shaft parts can be reduced, and an angle can be formed between the first clamping arm 310 and the second clamping arm 320, so as to form a shear structure at the clamping area, and to clamp and release the outer tube 810.

It should be noted that a space between mounting grooves of two rotating shafts is taken as a length of a first rod; a length of the first clamping arm 310 is taken as a length of a second rod; and a length of the second clamping arm 320 is taken as a length of a third rod, wherein the length of the first rod length is smaller than the sum of the lengths of the second rod and third rod, so that the thread gear support 300, the first clamping arm 310, and the second clamping arm 320 together compose a three-rod mechanism with the dead point position, The first rod, the second rod, and the third rod can be collinear temporarily by the elastic deformation of the thread gear support 300, the first clamping arm 310, or the second clamping arm 320. After the balance is broken, the first clamping arm 310 and the second clamping arm 320 will be deflected relative to the thread gear support 300 around the pivot shaft, so that the angle will form between the first clamping arm 310 and the second clamping arm 320, and at this state the locking state or the unlocking state can be reached.

In the unlocking state, an opening is formed on one side of the clamping area, wherein the clamped part of the second surgical instrument enters the clamping area through the opening along the first direction, and the first clamping arm 310 and the second clamping arm 320 are pushed to simultaneously switch to the locking state, so that the opening degree of the opening is reduced or closed; and when the clamped part, the first clamping arm 310, or the second clamping arm 320 is operated in a direction opposite to the first direction, the first clamping arm 310 and the second clamping arm 320 are simultaneously switched to the unlocking state, so that the clamped part is removed via the opening. When it is required to lock, the clamped part is inserted into the clamping area via the opening, and the first clamping arm 310 and the second clamping arm 320 can reach the locking state by toggling and pressing smoothly. When unlocking, it is only required to lift and pull the clamped part of the second surgical instrument, or to toggle the first clamping arm 310 and the second clamping arm 320 in a reverse direction, so as to drive the first clamping arm 310 and the second clamping arm 320 to swing and rotate to the unlocking state reversely, which is easy to operate, can be operated by the single hand, and does not require to change the position of the hand, so that the manipulation is more convenient.

Referring to FIG. 7, taking the second surgical instrument as the thread lock-cut mechanism 800 as an example, the outer tube 810 is coaxial with the endoscope working cavity 401 of the endoscope handle 400 in the locking state, so as to avoid the outer tube 810 from bending, so that the pulling threads inside the outer tube 810 can be pulled back smoothly.

As shown in FIG. 4, FIG. 5, FIG. 6, FIG. 7, and FIG. 8, the first clamping arm 310 is provided with the first position limitation groove 312, and the second clamping arm 320 is provided with the second position limitation groove 322 opposite to the first position limitation groove 312, wherein the clamping area is formed between the first position limitation groove 312 and the second position limitation groove 322. In the locking state, the thread gear support 300 squeezes the first clamping arm 310 and the second clamping arm 320 to deflect to the first direction (referring to a direction shown in FIG. 8), and the outer tube 810 (the clamped part) of the thread lock-cut mechanism 800 (the second surgical instrument) is clamped tightly between the first position limitation groove 312 and the second position limitation groove 322. In the unlocking state, the thread gear support 300 squeezes the first clamping arm 310 and the second clamping arm 320 to deflect to the second direction (referring to b direction shown in FIG. 8), so as to enlarge the opening degree of the opening between the first position limitation groove 312 and the second position limitation groove 322. When the first clamping arm 310 and the second clamping arm 320 are relatively straight, the first clamping arm 310 and the second clamping arm 320 reach a balance point. the operator can break the balance with the operation of the single hand, so that the first clamping arm 310 and the second clamping arm 320 deflect simultaneously, thereby realizing the locking and unlocking.

In an optional embodiment, when the first position limitation groove 312 is spliced with the second position limitation groove 322, and the axes are collinear, after the first clamping arm 310 and the second clamping arm 320 reach the dead point position and cross the dead point position towards a direction, the first clamping arm 310 and the second clamping arm 320 are limited by the locking and position limitation structure 304, and the outer tube 810 (the clamped part) of the thread lock-cut mechanism 800 (the second surgical instrument) is clamped tightly between the first position limitation groove 312 and the second position limitation groove 322.

As shown in FIG. 6, in an optional embodiment, the thread gear support 300 is provided with the locking and position limitation structure 304, or the first clamping arm 310 and/or the second clamping arm 320 are provided with the locking and position limitation structure 304, wherein the locking and position limitation structure 304 is configured to prevent the first clamping arm 310 and the second clamping arm 320 from continuing to deflect to the first direction during the locking state.

When the thread gear support 300 is provided with the locking and position limitation structure 304, at least one of the first clamping arm 310 and the second clamping arm 320 can abut against the locking and position limitation structure 304 in the locking state, so as to limit a maximum position of the first clamping arm 310 and the second clamping arm 320 deflecting towards the first direction. On the one hand, it can avoid the first clamping arm 310 and the second clamping arm 320 from swinging and rotating excessively, and on the other hand, it can avoid the outer tube 810 between the first position limitation groove 312 and the second position limitation groove 322 from being damaged due to excessive clamping and compression.

When the first clamping arm 310 or the second clamping arm 320 is provided with the locking and position limitation structure 304, or the first clamping arm 310 and the second clamping arm 320 are both provided with the locking and position limitation structure 304, the positions of the first clamping arm 310 and the second clamping arm 320 can be limited from each other by the locking and position limitation structure 304 in the locking state, so as to limit the maximum position of the first clamping arm 310 and the second clamping arm 320 deflecting towards the first direction.

A final note is as follows. The above embodiments are used only to illustrate the technical solutions of the present disclosure, and are not intended to be a limitation thereof. Although the present disclosure is described in detail with reference to the foregoing embodiment, those of ordinary skill in the art shall be understood, who can still modify the technical solutions recorded in the foregoing embodiments, or replace partial or all of the technical features therein with equivalent replacements; and these modifications or replacements do not take the essence of the corresponding technical solutions out of the scope of the technical solutions of the embodiments of the present disclosure.

What is claimed is:

1. A suture tightening device, comprising: a first thread take-up wheel, a second thread take-up wheel, and a thread gear support detachably connected to an endoscope handle, wherein the first thread take-up wheel is arranged at a space from the second thread take-up wheel, and the first thread take-up wheel and the second thread take-up wheel are separately in rotatable connection to the thread gear support;

wherein the thread gear support is connected with a bandage, and the bandage is bound to the endoscope handle.

2. The suture tightening device according to claim 1, wherein the first thread take-up wheel and the second thread take-up wheel both comprise: a gear body, a first gear disk, and a second gear disk, wherein the gear body, the first gear disk, and the second gear disk are arranged coaxially, wherein the first gear disk is arranged at a space from the second gear disk; the first gear disk and the second gear disk are separately connected to the gear body; and a thread winding groove is formed between the first gear disk and the second gear disk.

3. The suture tightening device according to claim 2, wherein the first thread take-up wheel and/or the second thread take-up wheel are provided with a thread clamping groove.

4. The suture tightening device according to claim 2, wherein the first thread take-up wheel and/or the second thread take-up wheel are provided with a plurality of position limitation parts, and the plurality of position limitation parts are arranged at intervals around a gear shaft.

5. The suture tightening device according to claim 4, wherein elastic position limitation members are mounted on the thread gear support; the elastic position limitation members are fitted to the position limitation parts; and the elastic position limitation members tend to keep fit with the position limitation parts.

6. The suture tightening device according to claim 5, wherein the elastic position limitation members support the first thread take-up wheel and the second thread take-up wheel, so as to prevent the first thread take-up wheel and the second thread take-up wheel from rotating back, and to keep sutures to be tightened extending from the endoscope handle to the first thread take-up wheel and the second thread take-up wheel respectively;

the position limitation parts are provided with beveled surfaces, wherein when the first thread take-up wheel or the second thread take-up wheel is rotated to tighten the sutures, the beveled surfaces push the elastic position limitation members, so that the elastic position limitation members remove from the position limitation parts; or when the elastic position limitation members incline along a circumference of the thread take-up wheel, and the first thread take-up wheel or the second thread take-up wheel is rotated to tighten the sutures, the position limitation parts push the elastic position limitation members, so that the elastic position limitation members slip out relative to the position limitation parts.

7. The suture tightening device according to claim 1, wherein an angle exists between an axis of the first thread take-up wheel and an axis of the second thread take-up wheel, and a bisector of the angle between the axis of the first thread take-up wheel and the axis of the second thread take-up wheel intersects an axis of an endoscope working cavity of the endoscope handle.

8. The suture tightening device according to claim 1, wherein a first clamping arm and a second clamping arm are movably mounted on the thread gear support, and a clamping area is formed between the first clamping arm and the second clamping arm.

9. The suture tightening device according to claim 8, wherein the first clamping arm is provided with a first tooth part; the second clamping arm is provided with a second tooth part fitted to the first tooth part; the first tooth part cooperates with the second tooth part; and the clamping area is formed between the first tooth part and the second tooth part.

10. The suture tightening device according to claim 8, wherein one end of the first clamping arm and one end of the second clamping arm are separately pivoted to the thread gear support, and the other end of the first clamping arm is opposite to the other end of the second clamping arm to form the clamping area.

11. The suture tightening device according to claim 8, wherein the thread gear support is elastic, and the thread gear support squeezes the first clamping arm and the second clamping arm, so that the first clamping arm and the second clamping arm tend to form an angle.

12. The suture tightening device according to claim 8, wherein in an unlocking state, an opening is formed on one side of the clamping area, wherein a clamped part of a second surgical instrument enters the clamping area through the opening along a first direction, and the first clamping arm and the second clamping arm are pushed to simultaneously switch to a locking state, so that an opening degree of the opening is reduced or closed; and when the clamped part, the first clamping arm, or the second clamping arm is operated in a direction opposite to the first direction, the first clamping arm and the second clamping arm are simultaneously switched to the unlocking state, so that the clamped part is removed via the opening.

13. The suture tightening device according to claim 12, wherein the first clamping arm is provided with a first position limitation groove; the second clamping arm is provided with a second position limitation groove opposite to the first position limitation groove; and the clamping area is formed between the first position limitation groove and the second position limitation groove, wherein in the locking state, the thread gear support squeezes the first clamping arm and the second clamping arm to deflect to the first direction, and the second surgical instrument is clamped between the first position limitation groove and the second position limitation groove; and in the unlocking state, the thread gear support squeezes the first clamping arm and the second clamping arm to deflect to a second direction, so as to enlarge an opening degree of the clamping area between the first position limitation groove and the second position limitation groove.

14. The suture tightening device according to claim 12, wherein the thread gear support is provided with a locking and position limitation structure, or the first clamping arm and/or the second clamping arm are provided with the locking and position limitation structure, wherein the locking and position limitation structure is configured to prevent the first clamping arm and the second clamping arm from continuing to deflect to the first direction during the locking state.

15. The suture tightening device according to claim 8, wherein the thread gear support is further provided with a crossbar, and the crossbar is provided with an avoiding groove, wherein the avoiding groove is configured to accommodate a second surgical instrument, and/or to prevent the second surgical instrument from continuing to move to a first direction.

16. The suture tightening device according to claim 10, wherein the thread gear support is elastic, and the thread gear support squeezes the first clamping arm and the second clamping arm, so that the first clamping arm and the second clamping arm tend to form an angle.

17. The suture tightening device according to claim 13, wherein the thread gear support is provided with a locking and position limitation structure, or the first clamping arm and/or the second clamping arm are provided with the locking and position limitation structure, wherein the locking and position limitation structure is configured to prevent the first clamping arm and the second clamping arm from continuing to deflect to the first direction during the locking state.

* * * * *